United States Patent
Knittel et al.

(10) Patent No.: US 12,042,153 B2
(45) Date of Patent: Jul. 23, 2024

(54) METHOD FOR PRODUCING A TRAY FOR STORING ANEURYSM CLIPS, AND TRAY FOR STORING ANEURYSM CLIPS

(71) Applicant: Aesculap AG, Tuttlingen (DE)

(72) Inventors: Timo Knittel, Wurmlingen (DE); Volker Huber, Mühlheim/Stetten (DE)

(73) Assignee: Aesculap AG, Tuttlingen (DE)

( * ) Notice: Subject to any disclaimer, the term of this patent is extended or adjusted under 35 U.S.C. 154(b) by 664 days.

(21) Appl. No.: 17/270,103

(22) PCT Filed: Aug. 28, 2019

(86) PCT No.: PCT/EP2019/072967
§ 371 (c)(1),
(2) Date: Feb. 22, 2021

(87) PCT Pub. No.: WO2020/043778
PCT Pub. Date: Mar. 5, 2020

(65) Prior Publication Data
US 2021/0169492 A1    Jun. 10, 2021

(30) Foreign Application Priority Data
Aug. 31, 2018   (DE) ...................... 10 2018 121 372.7

(51) Int. Cl.
*A61B 17/122*   (2006.01)
*A61B 17/00*   (2006.01)
(Continued)

(52) U.S. Cl.
CPC ............ *A61B 17/1222* (2013.01); *B21D 5/00* (2013.01); *B23K 26/38* (2013.01);
(Continued)

(58) Field of Classification Search
CPC ........ A61B 17/1222; A61B 2017/1225; A61B 2050/3008; A61B 50/33;
(Continued)

(56) References Cited

U.S. PATENT DOCUMENTS 4,519,501 A   5/1985   Cerwin
4,541,992 A   9/1985   Jerge et al.
(Continued)

FOREIGN PATENT DOCUMENTS

CN   107530136 A   1/2018
DE   102009000926 A1   10/2010
(Continued)

OTHER PUBLICATIONS

Written Opinion received in Application No. PCT/EP2019/072967 received in Application No. Nov. 28, 2019, 11 pages.
(Continued)

*Primary Examiner* — Rafael A Ortiz
(74) *Attorney, Agent, or Firm* — Christopher A. Rothe; Culhane PLLC

(57) ABSTRACT

A method for producing a tray for storing aneurysm clips, in which a metal plate is equipped with perforations. The perforations are produced by laser cutting. The plate with the perforations is reshaped by bending to form a corrugated sheet or a sheet with trapezoidal corrugations. The sheet has at least one channel-like indentation for storing aneurysm clips. A tray for storing aneurysm clips includes a corrugated sheet or a sheet with trapezoidal corrugations equipped with laser-cut perforations. The corrugated sheet or sheet with trapezoidal corrugations has at least one channel-like indentation.

2 Claims, 7 Drawing Sheets

(51) Int. Cl.
    *A61B 50/30*     (2016.01)
    *A61B 50/33*     (2016.01)
    *B21D 5/00*     (2006.01)
    *B23K 26/38*     (2014.01)

(52) U.S. Cl.
    CPC ............... *A61B 2017/00526* (2013.01); *A61B 2050/3008* (2016.02); *A61B 50/33* (2016.02)

(58) Field of Classification Search
    CPC .. A61B 2017/00526; A61B 2017/0416; A61B 2017/0479; A61B 17/06; B21D 5/00
    USPC ........ 206/339–341, 438, 564, 363–366, 570, 206/571, 210
    See application file for complete search history.

(56) References Cited

U.S. PATENT DOCUMENTS

| | | | |
|---|---|---|---|
| 4,928,821 A | | 5/1990 | Belko, Jr. |
| 5,441,709 A | | 8/1995 | Berry, Jr. |
| 5,909,179 A | | 6/1999 | Hiltman |
| 8,267,246 B2 * | | 9/2012 | Bettenhausen ........ A61B 50/30 206/439 |
| 10,575,933 B2 | | 3/2020 | Berg et al. |
| 2014/0069841 A1 * | | 3/2014 | Pizzato ................. B25H 3/026 206/570 |
| 2015/0010440 A1 | | 1/2015 | Roudebush et al. |

FOREIGN PATENT DOCUMENTS

| | | | | |
|---|---|---|---|---|
| EP | 3042626 A1 | 7/2016 | | |
| FR | 2898277 A1 | 9/2007 | | |
| WO | 2011003069 A2 | 1/2011 | | |
| WO | 2013119850 A1 | 8/2013 | | |
| WO | WO-2013119850 A1 * | 8/2013 | ............... A61L 2/26 |
| WO | 2016142331 A1 | 9/2016 | | |

OTHER PUBLICATIONS

Office Action received in Chinese Application No. 201980050541.6 dated Oct. 19, 2021, with translation, 14 pages.
Search Report received in Chinese Application No. 2019800505416 dated Oct. 11, 2021, with translation, 6 pages.
German Search Report received in Application No. 10 2018 121 372.7 dated Jun. 3, 2019, 11 pages.
International Search Report received in Application No. PCT/EP2019/072967 dated Nov. 28, 2019, 6 pages.

* cited by examiner

METHOD FOR PRODUCING A TRAY FOR STORING ANEURYSM CLIPS, AND TRAY FOR STORING ANEURYSM CLIPS

CROSS-REFERENCE TO RELATED APPLICATIONS

This application is the United States national phase entry of International Application No. PCT/EP2019/072967, filed Aug. 28, 2019, and claims the benefit of priority of German Application No. 10 2018 121 372.7, filed Aug. 31, 2018. The contents of International Application No. PCT/EP2019/072967 and German Application No. 10 2018 121 372.7 are incorporated by reference herein in their entireties.

FIELD

The present invention relates to a method for producing a tray made at least partly from metal for storing aneurysm clips, especially to a method in which firstly a metal plate is provided which is subsequently equipped with perforations or, resp., a hole pattern. The present invention further relates to a corresponding tray for storing aneurysm clips.

BACKGROUND

On the one hand, trays for storing aneurysm clips made from plastic material are known. It is the problem of those trays that, in the case of plastic material, complete drying after washing or sterilizing of the trays is only possible with great effort (i.e., with long drying time and/or high drying energy expenditure).

On the other hand, trays for storing aneurism clips which are made from metal are known already. It is the problem of those hitherto existing metal trays that manufacture thereof is too intricate and cost-intensive.

SUMMARY

Therefore, it is the object of the present invention to provide a tray for storing aneurysm clips that can be sterilized as easily as possible and a corresponding manufacturing method that is as simple as possible by means of which such tray for storing aneurysm clips can be manufactured.

Firstly, a metal plate is provided which is subsequently equipped with perforations. The plate is preferably made from stainless steel (e.g., stainless steel 1.4301 or X5CrNi18-10, AISI 304, V2A, SUS304). Alternatively, the plate may also be made from a titanium alloy or from anodized aluminum. Preferably, the plate has a thickness ranging from 0.5 mm to 2.0 mm, especially a thickness of 0.8 mm. According to the invention, the perforations are produced by laser cutting, and the plate equipped with the perforations is reshaped by means of bending to form a corrugated sheet or a sheet with trapezoidal corrugations which sheet has at least one channel-like indentation for storing aneurysm clips.

The method according to the invention offers the advantage that a holder for aneurysm clips that can easily be sterilized is produced by merely three steps.

The use of a metal plate and the introduction of perforations or holes by means of laser cutting offers plural advantages. On the one hand, the perforation ratio, that is the ratio of the hole surface to the total surface, can generally be increased by laser cutting, as in this way a substantially more intricate perforation and a more efficient perforation pattern can be fabricated than it is possible by punching, for example. On the other hand, the use of a metal plate as compared to known plastic trays also allows such higher perforation ratio without any losses in the inherent stability of the tray having to be feared. Due to the higher perforation ratio, it is possible to minimize the surface on which liquid may collect.

In accordance with one aspect of the invention, at least one plug-in wall can be mounted, preferably without using tools, into the at least one channel-like indentation of the corrugated or trapezoidal sheet, the plug-in wall laterally delimiting or subdividing the channel-like indentation and being dismountable, preferably without using tools, from the corrugated sheet or trapezoidal sheet.

The at least one channel-like indentation according to the invention may be designed basically with or without end faces. If it is designed without an end face, a compartment can be produced by means of plug-in walls dismountable without using tools. Such compartment or a channel-like indentation designed with end faces can be subdivided by means of at least one plug-in wall dismountable without using tools. Preferably, the plug-in walls are designed so that they interact with part of the perforations for connecting to the corrugated or trapezoidal sheet. For example, they can be connected to corresponding perforations via clip connections.

According to one aspect of the invention, the perforations can be produced by subdividing interfaces defining the individual perforations firstly into subareas, subsequently grouping all subareas of all interfaces corresponding to their orientation into at least two groups, and producing each of the at least two groups of the subareas of all perforations finally en bloc or in one piece by means of laser cutting. In other words, each individual perforation is not produced in one coherent step. Rather, for example in the case of perforations having rectangular recesses or slits, firstly all edges of all recesses which extend in a first direction are cut, and subsequently all edges of all recesses which extend in a second direction perpendicularly to the first direction are cut. This helps avoid time-consuming changes of direction of the laser during manufacture. Moreover, this process may also be advantageous as regards avoiding local thermal deformations caused by heat. The production of the perforations by means of a laser generates heat which, in turn, may cause the plate to deform. If each individual perforation initially is cut only partially, the locally introduced amount of heat is not as large as when a whole perforation is cut. By means of tolerances it can be predetermined in how far the subareas of the interfaces have to be equally oriented. Thus, it is not necessary for the corresponding subareas to be exactly equally oriented.

According to one aspect of the invention, the plate can be clamped at two opposite ends, before the perforations are produced. In other words, the plate can be perforated in a clamped condition. The deformations produced by heat can be counter-acted by clamping.

A tray for storing aneurysm clips according to the invention includes a corrugated sheet or sheet with trapezoidal corrugations provided with laser-cut perforations and having at least one channel-like indentation.

According to one aspect of the invention, the maximum width of the perforations is less than 1 mm, preferably it ranges from 0.3 mm to 1.0 mm, especially it ranges from 0.5 mm to 0.8 mm. This ensures that the tray, on the one hand, can be rinsed easily and properly with washing liquid and/or sterilizing fluid (e.g., steam) and, on the other hand, the aneurysm clips neither can fall through the perforations nor can get entangled or get jammed or stuck in the same.

According to one aspect of the invention, the maximum land width or the distance between neighboring perforations is less than 0.8 mm, preferably it ranges from 0.3 mm to 0.8 mm, especially from 0.5 mm to 0.7 mm. This ensures that the tray offers little surface area for any liquid to collect, while it has sufficient dimensional stability.

According to one aspect of the invention, the tray may include at least one plug-in wall connected to the corrugated sheet or sheet with trapezoidal corrugations and being dismountable without using tools, which plug-in wall delimits or subdivides the channel-like indentation. The dismountability without using tools enables the size of a tray for aneurysm clips to be easily manually varied.

According to one aspect of the invention, the at least one plug-in wall can include at least one projection and particular perforations can be adapted to the shape of said at least one projection so that the at least one projection can be inserted only into said particular perforations. Thus, only particular sizes, for example standardized sizes, can be ensured to be admitted for the aneurysm clip holder.

According to one aspect of the invention, at least particular perforations can be of equal size and of cuboid shape in each case. "Cuboid" in this context means that the perforations have a substantially rectangular contour. Said cuboid perforations may be arranged in rows parallel to each other and can be oriented with their respective longitudinal axis in parallel to the direction of extension of the rows. Each row may be offset against at least one adjacent row in the direction of extension of the rows by half a perforation length. In other words, the uniformly cuboid perforations may be arranged like bricks of a central stretcher of a brickwork. In contrast to a chessboard-like arrangement, the offset distribution of the perforations offers the advantage that it impedes expansion of individual perforations.

According to one aspect of the invention, the tray may include at least one holder cover which is connected to the corrugated sheet or sheet with trapezoidal corrugations and is dismountable without using tools, the holder cover covering the channel-like indentation at least in portions. By means of such holder cover, the holder for aneurysm clips can be closed to the outside so that an aneurysm clip accommodated in the holder is secured within the holder. Moreover, information about the respective aneurysm clip can advantageously be attached to the outside of the holder cover.

BRIEF DESCRIPTION OF THE DRAWING FIGURES

Hereinafter, the present invention shall be described in detail by means of preferred embodiments with reference to the attached drawings, wherein.

Like or functionally equivalent features are provided with like reference numerals in the individual figures.

DETAILED DESCRIPTION

Figure 1:
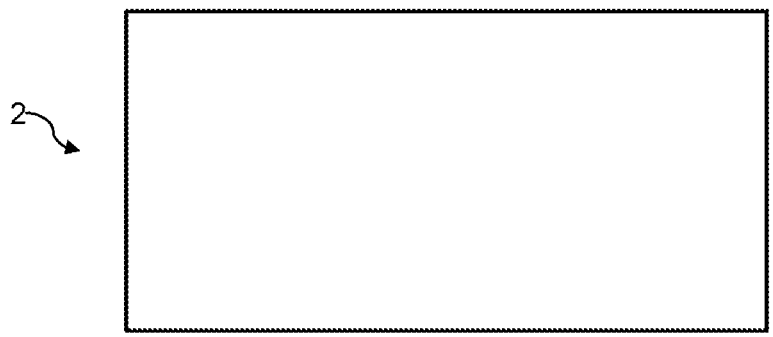
FIG. 1 shows a top view onto a metal plate.
Figure 2:
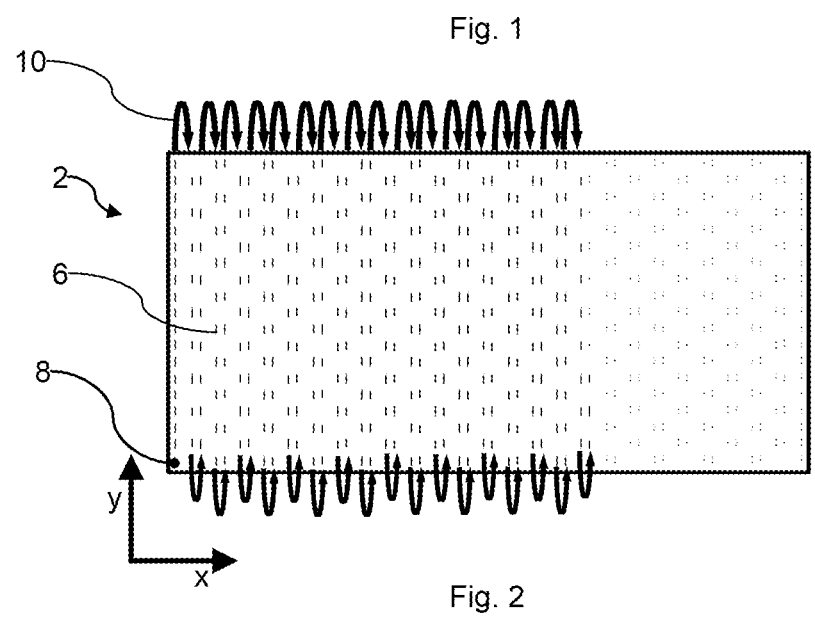
FIG. 2 shows a top view onto the plate shown in FIG. 1 in which part of a first group is cut at interfaces by perforations.
Figure 3:
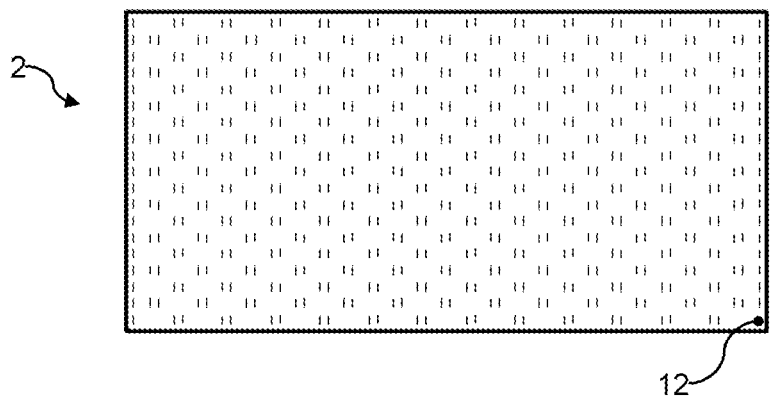
FIG. 3 shows a top view of the plate shown in FIGS. 1 and 2 in which the entire first group is cut at interfaces by the perforations.
Figure 4:
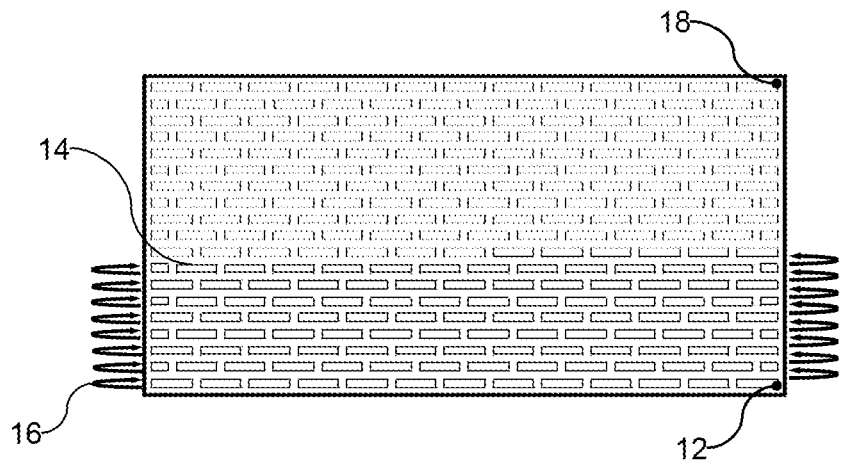
FIG. 4 shows a top view onto the plate shown in FIGS. 1 to 3, in which part of a second group is cut at interfaces by the perforations.

FIG. 1 illustrates a top view onto a metal plate 2 which has a substantially rectangular outline. In order to equip the plate 2 with perforations 4 (see FIG. 5), initially first edges or interfaces 6 of the perforations 4 are cut into the plate 2 (see FIGS. 2 and 3) by means of a laser (not shown). A feature that is common to the first interfaces 6 is that all of them extend in a direction y. So as to cut the first interfaces 6 as efficiently as possible, laser cutting is started at a starting point 8 in one corner of the plate 2, and the individual first interfaces 6 are cut by pulsed driving of the laser when the laser scans the plate 2 in a serpentine-like manner (see arrows 10).

After having cut all of the first interfaces 6 and the laser being provided at the intermediate point 12, second edges or interfaces 14 are cut. A feature that is common to the second interfaces 14 is that all of them extend in a direction x perpendicular to the direction y. Starting from the intermediate point 12 which is equally located in a corner of the plate 2, the individual second interfaces 14 are equally cut by pulsed driving of the laser when the laser scans the plate 2 in a serpentine-like manner (see arrows 16).

Pulsed driving of the laser in this context means that the laser operates substantially with high power when it intersects a perforation line. High power means that the power is so high that the material to be cut is cut, at the respective cutting speed corresponding to the feeding speed of the laser, over the complete thickness of the material. When the laser is moved between two perforation lines, the laser is not completely turned off, but the power of the laser is merely reduced, to be specific so far that the surface of the sheet is not damaged. As the laser is not turned off completely between two cutting operations of two perforation lines, the time until it returns to high power is reduced. In this way, the cutting speed or the feeding speed of the laser can be significantly increased vis-à-vis the case in which the laser is always turned off completely between two cutting operations.

Figure 5:
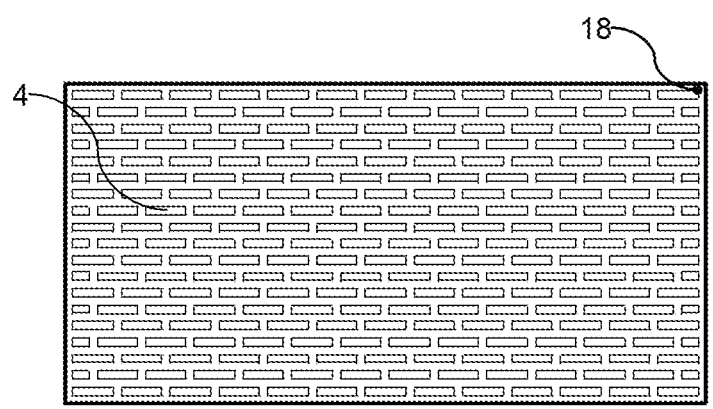
FIG. 5 shows a top view onto the plate shown in FIGS. 1 to 4 in which all interfaces are cut by the perforations.
Figure 6:
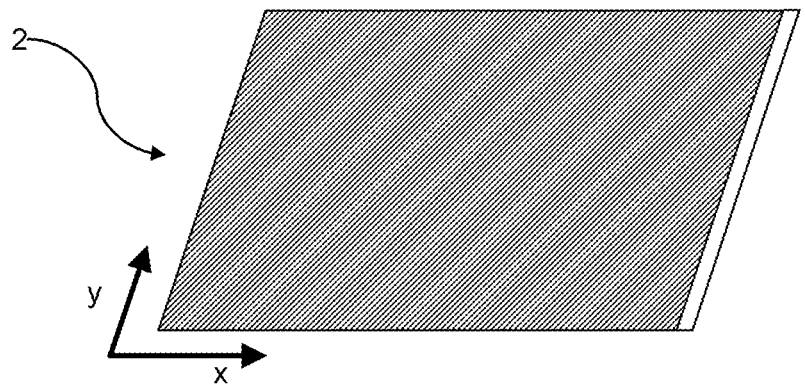
FIG. 6 shows a perspective view of the perforated plate illustrated in FIG. 5

After having cut all of the second interfaces 14 and the laser is at the final point 18, the laser cutting of the perforations 4 is completed (see FIGS. 5 and 6).

According to the method illustrated in FIGS. 2 to 5, firstly all short sides of the perforations 4 each having a substantially rectangular contour are cut, before the corresponding long sides are cut. As an alternative, it is also possible that firstly all of the long sides are cut, before all of the short sides are cut.

As illustrated in FIG. 6, only subareas of the plate 2 may be perforated (see hatched part of the plate 2). For example, a rim may be left free from perforations.

In FIGS. 7 to 14, no perforations are shown for reasons of clarity.

Figure 7:
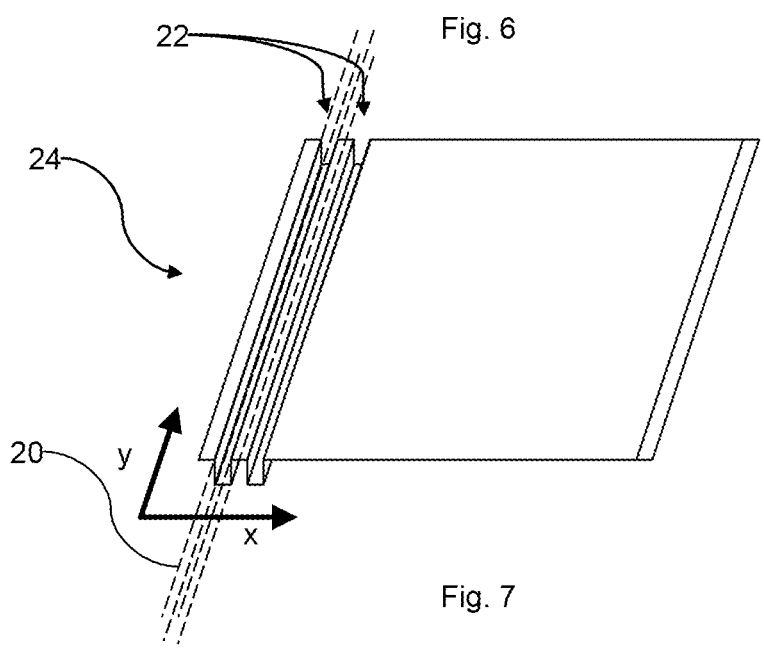
FIG. 7 shows a perspective view of the plate illustrated in FIG. 6 which has been provided with two channel-like indentations by bending.
Figure 8:
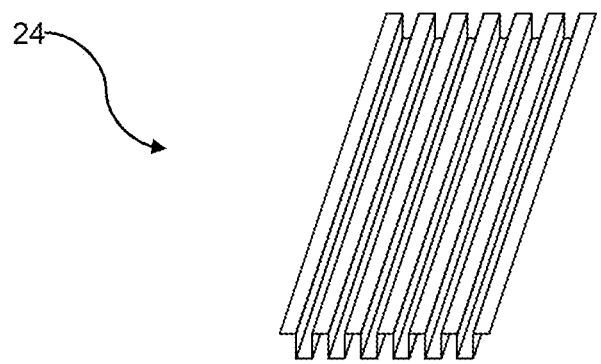
FIG. 8 shows a perspective view of the plate illustrated in FIG. 6 which has been reshaped by bending to form a trapezoidal sheet.

After laser cutting, the plate 2 equipped with perforations 4 is repeatedly bent about edges 20 parallel to the direction y such that a channel-like indentation 22 is formed (see FIG. 7). This procedure is repeated until the whole plate 2 includes channel-like indentations 22 over its entire surface (see FIG. 8). The plate provided with the channel-like indentations 22 shall be referred to as sheet with trapezoidal corrugations 24 in the following.

Figure 9:
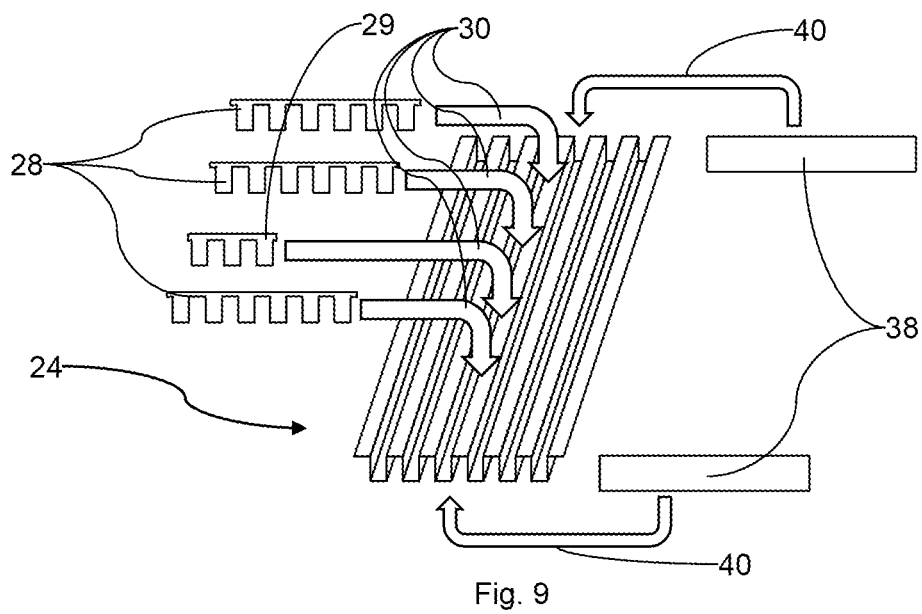
FIGS. 9 and 10 show perspective views of the trapezoidal sheet illustrated in FIG. 8 including plug-in walls and end walls.
Figure 10:
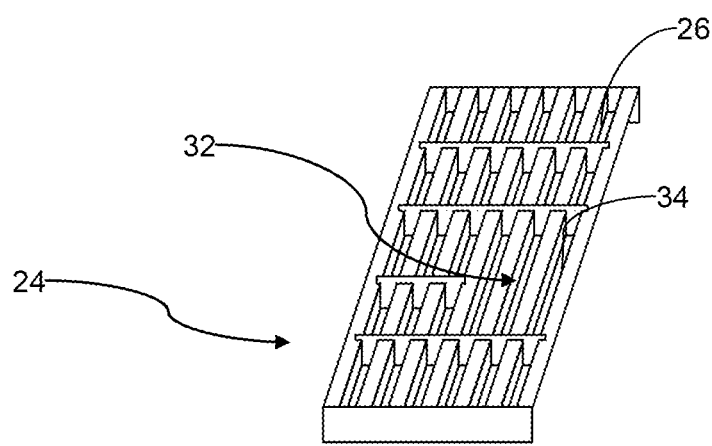
Figure 11:
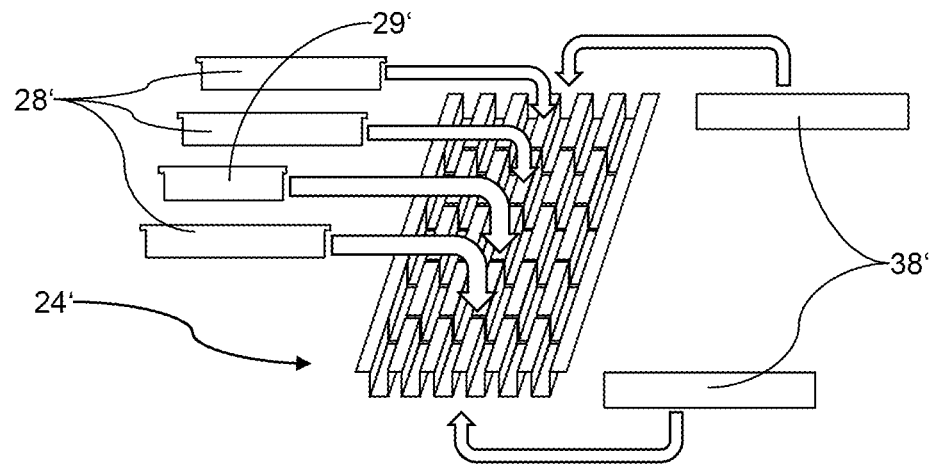
FIG. 11 shows a perspective view of an alternatively configured trapezoidal sheet including plug-in walls and end walls.
Figure 12:
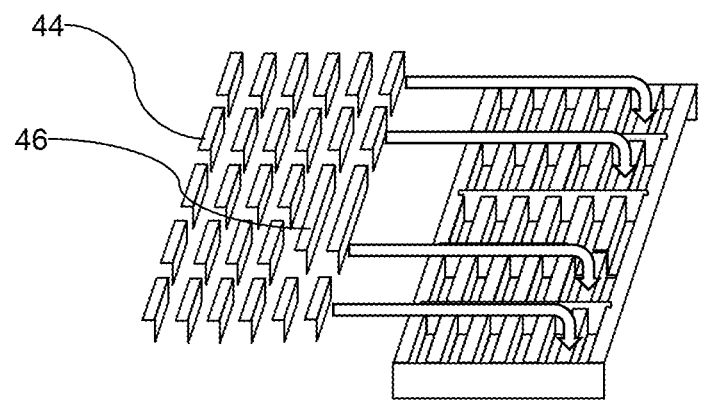
FIG. 12 shows a perspective view of the trapezoidal sheet illustrated in FIG. 11 including identification labels.

In order to produce defined aneurysm clip holders 26, plug-in walls 28 and 29 are inserted into the channel-like indentations 22 (see arrow 30 in FIG. 9). For larger aneurysm clips large aneurysm clip holders 34 are provided in part 32 of the sheet with trapezoidal corrugations 24. The plug-in walls 28 may be solid plates or may equally include perforations.

The plug-in walls 28 and 29 may be crenelated. This means that the plug-in walls 28 and, resp., 29 are designed so that subareas immerse into individual indentations 22 of the trapezoidal sheet 24 and that other subareas of the plug-in walls 28 and, resp., 29 connect the subareas immersing into different indentations 22. The plug-in walls 28 are designed to be longer than the plug-in wall 29, that means that a respective plug-in wall 28 has six crenelations and subdivides all of the six indentations 22 of the sheet with trapezoidal corrugations 24, whereas the short plug-in wall 29 has only three crenelations and subdivides only three out of the six indentations 22. By providing the short plug-in wall 29, the large aneurysm clip holders 34 can be formed in the indentations which are not subdivided by the plug-in wall 29.

In order to close ends of the channel-like indentations 22, end walls 38 that are disposed at the corrugated edges of the trapezoidal sheet 24 are provided (see arrows 40 in FIG. 9). Preferably, the end walls 38 are connected to the sheet with trapezoidal corrugations 24 by laser welding.

Instead of providing crenelated plug-in walls 28 and, resp., 29, it is also possible to manufacture the trapezoidal sheet from a slitted plate. The respectively resulting trapezoidal sheet 24' shown in FIGS. 11 to 13 includes slits 42 into which substantially rectangular plug-in walls 28' and, resp., 29' can be inserted.

Also, it is possible to provide slits which merely facilitate and, resp., improve the fastening of crenelated plug-in walls 28' and, resp., 29' in the sheet with trapezoidal corrugations 24.

Identification labels 44 and, resp., 46 are provided so that the aneurysm clip holders 26 and 34 can be labeled. For mounting the identification labels 44 and 46, they are attached from above to the sheet with trapezoidal corrugations 24 (see arrow 48 in FIG. 12). The identification labels 46 are configured to be long, i.e., they are only suited for labeling large aneurysm clip holders 34. The identification labels 44 are configured to be short and serve for labeling normal aneurysm clip holders 26. The identification labels 44 and 46 substantially are L profiles. When the identification labels 46 and, resp., 44 are attached to a corresponding aneurysm clip holder 26 or 34, one leg of the L profile extends along a sidewall of an aneurysm clip holder and the other leg of the L profile extends in the plane of the access opening of the aneurysm clip holder 26 or 34 next to the access opening. On the upper side of a respective labeling plate, a picture (not shown) of the aneurysm clip to be stored in the respective aneurysm clip holder 26 or 34 may be provided.

Figure 13:
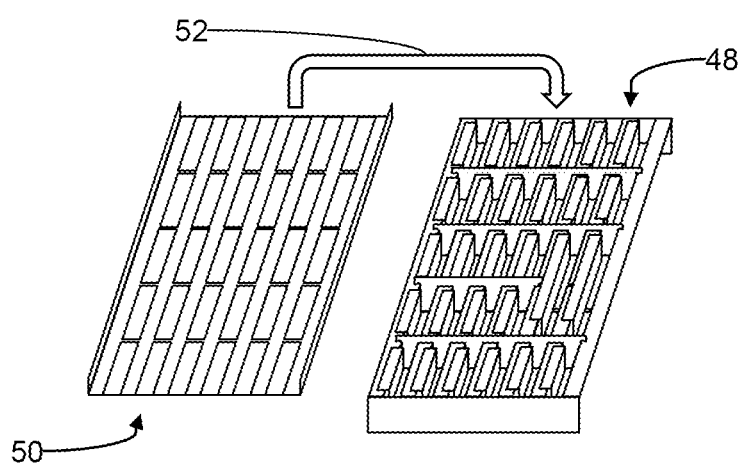
FIG. 13 shows a perspective view of a tray according to the invention having an open lid.

As illustrated in FIG. 13, the sheet with trapezoidal corrugations 24, the end walls 38, the plug-in walls 28 and, resp., 29 as well as the identification labels 44 and, resp., 46 form a tray 48 according to the invention.

Figure 14:
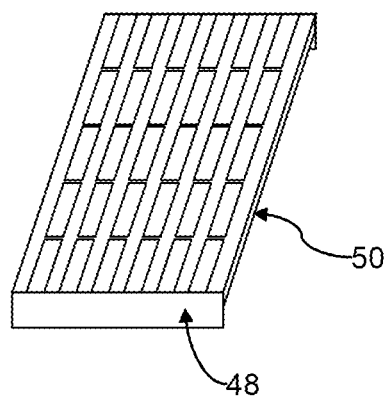
FIG. 14 shows a perspective view of the tray according to the invention having a closed lid.

As illustrated in FIGS. 13 and 14, the tray 48 can be closed with a lid 50 (see arrow 52 in FIG. 13). Preferably, the tray 48 is made from a sheet having a thickness of 0.8 mm and the lid 50 is made from a sheet having a thickness of 1 mm.

The embodiment of the tray for storing aneurysm clips according to the invention as illustrated in FIGS. 13 and 14 and described above constitutes merely one possible implementation of the invention.

Figure 15:
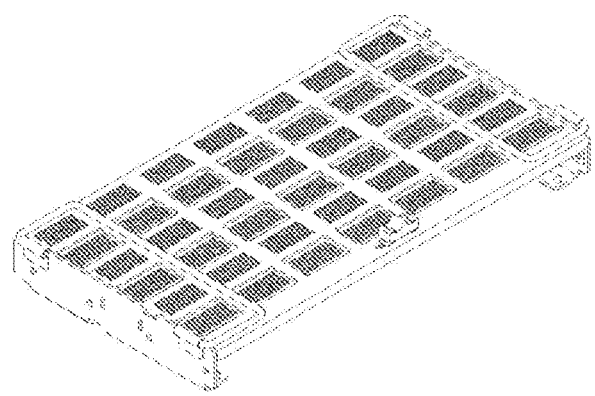
FIG. 15 shows a perspective view of another embodiment of the tray according to the invention having a closed lid.
Figure 16:
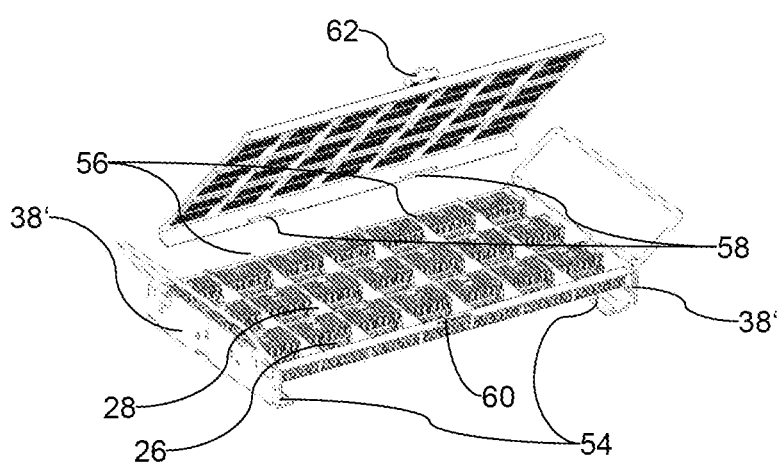
FIG. 16 shows a perspective view of the embodiment of the tray according to the invention illustrated in FIG. 15 having an open lid.

In accordance with another advantageous embodiment shown in FIGS. 15 and 16, the cut perforated sheet of FIG. 6 is cut into individual strips, and then each strip is bent into a channel-like indentation 22 with an adjacent holding surface for an identification label. A plurality of said elements configured in this way are assembled by means of laser welding to form a group. To the end faces of the channel-like indentations 22 end sheets or end walls 38' are welded so as to form a tray 24". The end walls 38' have pedestals 54 and holders 56 into which projections 58 of a lid 50' can be inserted, as well as a holder 60 for a closure member 62 that is provided at the lid 50' and serves for detachably fastening the lid 50' to the tray 24" and, in so doing, covering and thus closing the channel-like indentations 22. Plug-in walls 28 can be detachably introduced transversely to the channel-like indentations 22 to form plural separate aneurysm clip holders 26 for different aneurysm clips from the channel-like indentations 22. Preferably, the holding surfaces are slitted so that the plug-in walls 28 can be inserted from the top to the bottom of the channel-like indentations 22.

Figure 17:
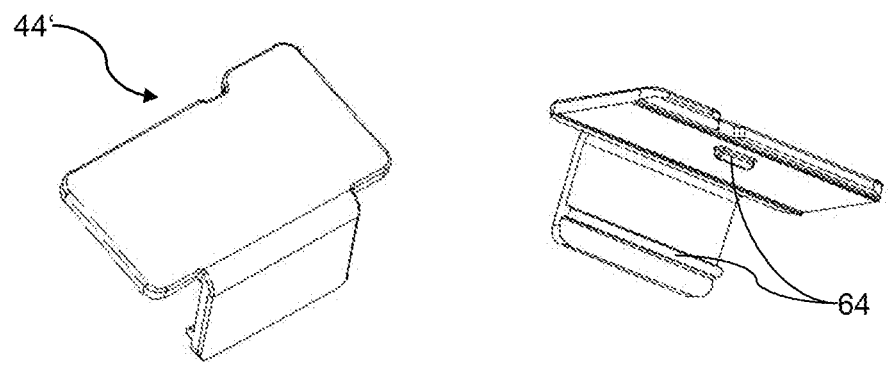
FIG. 17 shows perspective views of a short identification label.
Figure 18:
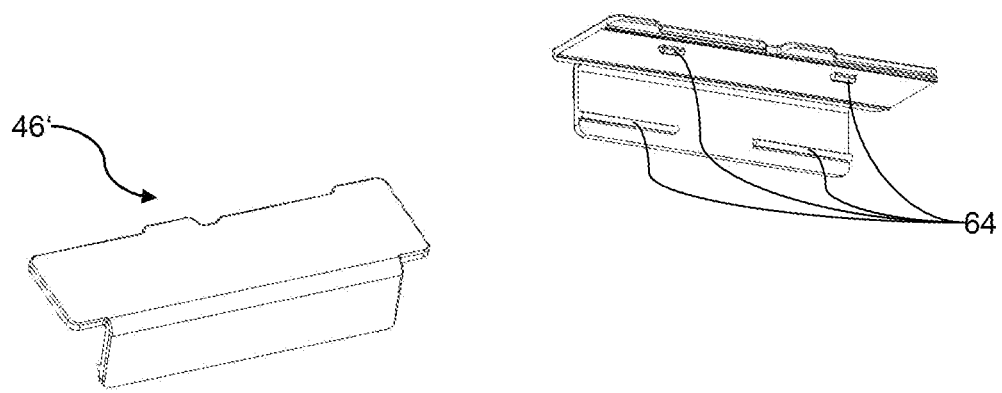
FIG. 18 shows perspective views of a long identification label.

In FIGS. 17 and 18, short and long identification labels 64 and, resp., 66 are shown. In order to be connectable to the corresponding sheet with trapezoidal corrugations 24" illustrated in FIG. 16, the identification labels 64 and, resp., 66 configured as L profiles include, at each of their legs, at least one projection 68 adapted to be clipped into corresponding recesses in the sheet with trapezoidal corrugations 24".

The invention claimed is:

1. A method for producing a tray for storing aneurysm clips, the tray being produced from a metal plate, the method comprising the steps of:
producing a plurality of perforations in the plate by laser cutting; and
reshaping the plate by bending to form a corrugated sheet with trapezoidal corrugations which has at least one channel indentation for storing aneurysm clips,
the perforations being produced by firstly subdividing interfaces which define the perforations into subareas, and by subsequently grouping the subareas of the interfaces corresponding to their orientation into at least two groups and by finally producing the at least two groups in each case en bloc by laser cutting.

2. A method for producing a tray for storing aneurysm clips, the tray being produced from a metal plate, the method comprising the steps of:
- producing a plurality of perforations in the plate by laser cutting;
- reshaping the plate by bending to form a corrugated sheet with trapezoidal corrugations which has at least one channel indentation for storing aneurysm clips; and
- mounting at least one plug-in wall into the at least one channel indentation of the corrugated sheet,
- the at least one plug-in wall laterally delimiting or subdividing the at least one channel indentation and being dismountable from the corrugated sheet,
- wherein the plate is clamped at two opposite ends prior to producing the perforations.

* * * * *